(12) United States Patent
Takase et al.

(10) Patent No.: US 7,358,356 B2
(45) Date of Patent: Apr. 15, 2008

(54) PROCESSES FOR PREPARATION OF ORGANIC COMPOUNDS

(75) Inventors: Mitsuru Takase, Niigata (JP); Takahiro Sagae, Kanagawa (JP); Hiroyuki Yazaki, Niigata (JP); Shigeo Mori, Niigata (JP); Daisuke Asanuma, Niigata (JP)

(73) Assignee: Asubio Pharma Co., Ltd., Tokyo (JP)

( * ) Notice: Subject to any disclaimer, the term of this patent is extended or adjusted under 35 U.S.C. 154(b) by 306 days.

(21) Appl. No.: 10/529,392

(22) PCT Filed: Oct. 2, 2003

(86) PCT No.: PCT/JP03/12662

§ 371 (c)(1),
(2), (4) Date: Mar. 28, 2005

(87) PCT Pub. No.: WO2004/031196

PCT Pub. Date: Apr. 15, 2004

(65) Prior Publication Data

US 2006/0058521 A1   Mar. 16, 2006

(30) Foreign Application Priority Data

Oct. 2, 2002   (JP)   ............................. 2002-290156

(51) Int. Cl.
*C07D 499/18* (2006.01)

(52) U.S. Cl. ...................................................... 540/310

(58) Field of Classification Search .................. 540/310
See application file for complete search history.

(56) References Cited

U.S. PATENT DOCUMENTS 5,703,068 A * 12/1997 Iwata et al. .................. 514/195

FOREIGN PATENT DOCUMENTS

| JP | 5-301882 | 11/1993 |
|----|----------|---------|
| WO | WO 92/03444 | 3/1992 |

* cited by examiner

*Primary Examiner*—Taofiq Solola
(74) *Attorney, Agent, or Firm*—Manelli Denison & Selter PLLC; Paul E. White

(57) ABSTRACT

The present invention provides a method for preparing an organic compound, which comprises a dehydration step of distilling off water from a polar organic solvent solution containing the organic compound and water to bring the concentration of water below a given level, wherein the dehydration step comprises distilling off water together with the polar organic solvent while adding a polar organic solvent to the solution, or comprises repeating several cycles of adding a polar organic solvent to the solution and then distilling off water together with the polar organic solvent. The present invention further provides the preparation of an organic compound, which enables efficient isolation of the target product in high isolated yield from a polar organic solvent solution containing the organic compound, water and, if necessary, a compound which produces, upon coming into contact with water or the like, a substance accelerating the decomposition of the organic compound.

5 Claims, No Drawings

PROCESSES FOR PREPARATION OF ORGANIC COMPOUNDS

This application is the national phase of international application PCT/JP03/12662 filed 2 Oct. 2003 which designated the U.S.

TECHNICAL FIELD

The present invention relates to a dehydration method for a polar organic solvent solution containing an unstable organic compound and water.

BACKGROUND ART

A compound having a β-lactam ring in its molecule (hereinafter referred to as a "β-lactam compound") is useful as an antibacterial agent with potent antibacterial activity. A wide variety of β-lactam compounds have been developed as antibacterial agents and various β-lactam compounds have been produced on an industrial scale.

Although such a β-lactam compound is characterized by having a β-lactam ring in its molecule, this β-lactam ring may be decomposed depending on the type of its substituent, the type of its condensed ring, and/or environmental conditions surrounding its solution (e.g., heat, the presence of water, the property thereof (acidic or alkaline)). For this reason, when β-lactam compounds are to be produced, as mild conditions as possible are selected for their production in order to prevent the compounds from becoming decomposed and causing side reactions during the production process.

For example, a β-lactam compound (4) useful as an antibacterial agent can be prepared by the reaction shown below.

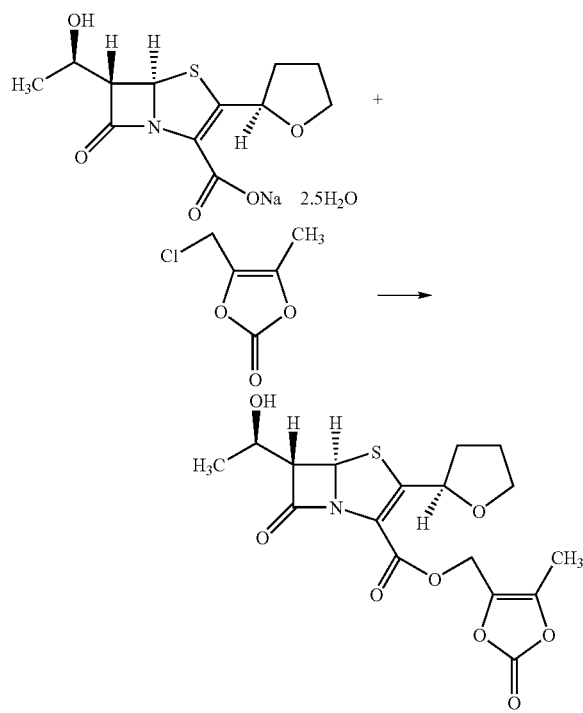

(4)

However, when carrying out the above reaction to prepare β-lactam compounds on an industrial scale, there is a problem arising from a significant reduction in isolated yield during the step of isolating the target β-lactam compound (4) from the resulting reaction solution.

DISCLOSURE OF THE INVENTION

The present invention has been made by taking into consideration the above situation, and aims to provide a method for preparing an organic compound (e.g., a β-lactam compound), which enables efficient isolation of the target product in high isolated yield.

The inventors of the present invention have made a detailed examination of the step where the target β-lactam compound (4) is isolated from the reaction solution obtained by the above reaction. As a result, the reason for the reduction in the isolated yield of the β-lactam compound (4) would be because in a dehydration step where water is distilled off together with THF from a reaction mixture containing the β-lactam compound (4), distillation reduces the liquid level and hence the highly concentrated solution remaining on the wall surface of the reaction vessel becomes decomposed due to being heated on the vessel wall surface.

In such a dehydration step where water is distilled off together with THF from a reaction solution containing the β-lactam compound (4), the inventors of the present invention have found that when THF and water are distilled off while adding THF to maintain the reaction solution at a constant level, it is possible to avoid the reduction in isolated yield resulting from the decomposition of the β-lactam compound (4). Likewise, in the case of solvent replacement from THF to ethanol (used as a crystallization solvent), they have also found that when THF is distilled off while adding ethanol to maintain the reaction solution at a constant level, it is possible to isolate the target product in high isolated yield. They have made further attempts to adapt such a technique to other cases and have completed the present invention.

Thus, the present invention provides a method for preparing an organic compound, which comprises a dehydration step of distilling off water from a polar organic solvent solution containing the organic compound and water to bring the concentration of water below a given level, wherein the dehydration step comprises distilling off water together with the polar organic solvent while adding a polar organic solvent to the above polar organic solvent solution, or comprises repeating several cycles of adding a polar organic solvent to the above polar organic solvent solution and then distilling off water together with the polar organic solvent.

In the method of the present invention, the above dehydration step is preferably followed by a crystallization step of distilling off the polar organic solvent from the resulting solution while supplementing the solution with a poor solvent for the organic compound so as to crystallize the organic compound. In this case, an alcohol solvent is preferred for use as a poor solvent.

In the method of the present invention, the organic compound is preferably a β-lactam compound, and more preferably a β-lactam compound of Formula (1):

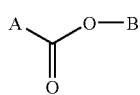

(1)

wherein A represents a condensed heterocyclic group having a β-lactam ring structure, and B represents an optionally substituted $C_1$-$C_{20}$alkyl group, an optionally substituted $C_2$-$C_{20}$alkenyl group, an optionally substituted $C_2$-$C_{20}$alkynyl group, an optionally substituted aryl group or an optionally substituted heterocyclic group.

In the method of the present invention, the polar organic solvent solution is preferably a reaction solution obtained by reacting a compound of Formula (2):

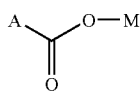

(2)

wherein A represents a condensed heterocyclic group having a β-lactam ring structure, and M represents a hydrogen atom or a metal atom, in a polar organic solvent, with a 4-halogenomethyldioxolenone compound of Formula (3):

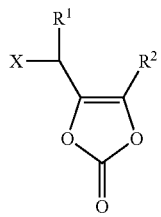

(3)

wherein $R^1$ and $R^2$ each independently represent a hydrogen atom, an optionally substituted $C_1$-$C_6$alkyl group or an optionally substituted phenyl group, or $R^1$ and $R^2$ may together form an optionally substituted $C_3$-$C_8$ring, and X represents a halogen atom, or a solution obtained by working up the reaction solution.

MODES FOR CARRYING OUT THE INVENTION

The method of the present invention will be further described in more detail below.

1) Polar Organic Solvent Solution

The method of the present invention comprises a dehydration step where a polar organic solvent solution containing an organic compound and water is distilled to remove water together with the polar organic solvent.

(a) Organic Compound

Although there is no particular limitation on the organic compound targeted by the method of the present invention, it may be an organic compound which is partially decomposed when exposed to long-term attack by heating in a water-containing organic solvent, especially an organic compound whose decomposition is accelerated depending on the property of water contained in the organic solvent, more specifically under acidic or alkaline conditions. Such an organic compound may be preferred for use in the method of the present invention.

As used herein, the term "decomposition" is intended to mean changing into a compound which is structurally different from the original one. This term encompasses elimination of substituent(s), conversion into a different skeleton, complete breakdown of the skeleton, etc. There is no particular limitation on the degree of decomposition; partial and complete decomposition of the original compound are both intended. In particular, in a case where the method of the present invention is applied to industrial processes, a very slight decrease in yield will affect the purity and product yield of final products. Thus, the method of the present invention is preferably used when 0.1% to several % of the organic compound is decomposed.

Examples of such an organic compound include β-lactam compounds having a β-lactam ring in their molecule; compounds having a hydroxy group protected with a hydrolyzable protecting group such as a tetrahydrofuryloxy group, a tetrahydropyranyloxy group, a t-butoxy group, a 1-ethoxyethoxy group, an acetoxy group, a trimethylsilyloxy group, a triphenylmethoxy group or a 2,2,2-trichloroethoxy group; acetal compounds; hemiacetal compounds; compounds having a C=N bond in their molecule; and compounds having an enolic hydroxy group protected with an acyl group.

Among these compounds, the method of the present invention is preferably used as part of the production process for β-lactam compounds.

β-Lactam compounds are known as active ingredients of β-lactam antibacterial agents. As long as they have a β-lactam ring in their molecule, β-lactam compounds are not limited in any way and include monocyclic compounds and condensed ring compounds. There is also no limitation on the type and number of substituents attached to the β-lactam ring. Among them, preferred are compounds whose molecule carries a condensed heterocyclic group having a β-lactam ring, and particularly preferred are compounds of the above Formula (1).

In the above Formula (1), A represents a condensed heterocyclic group having a β-lactam ring. The following may be mentioned as examples of such a condensed heterocyclic group having a β-lactam ring structure:

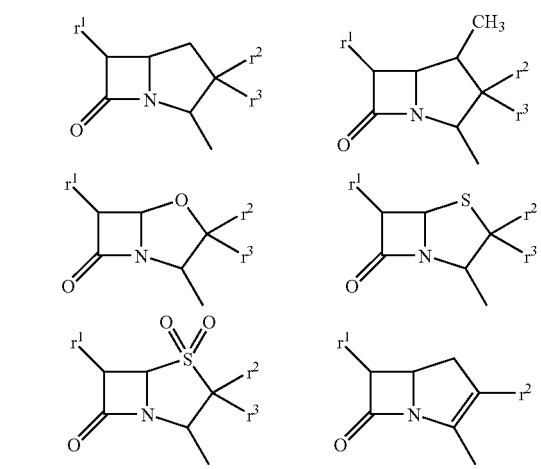

-continued

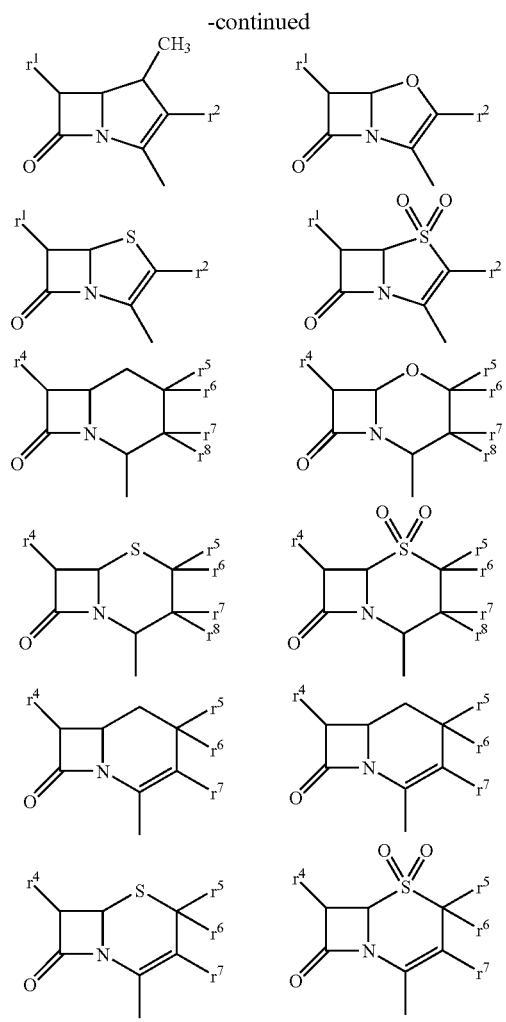

In the above formula, r¹ and r⁴ each represent a $C_1$-$C_6$alkyl group which may be substituted with $G^1$ or a benzoylamino group which may be substituted with $G^1$.

r², r³, r⁵, r⁶, r⁷ and r⁸ each independently represent a hydrogen atom, a $C_1$-$C_6$alkyl group which may be substituted with $G^1$, a $C_2$-$C_6$alkenyl group which may be substituted with $G^1$, a $C_2$-$C_6$alkynyl group which may be substituted with $G^1$, an aromatic hydrocarbon group which may be substituted with $G^1$ or a heterocyclic group which may be substituted with $G^1$.

In relation to the groups defined for r¹ to r⁸, examples of a $C_1$-$C_6$alkyl group in the $C_1$-$C_6$alkyl group which may be substituted with $G^1$ include a methyl group, an ethyl group, a n-propyl group, an isopropyl group, a n-butyl group, a sec-butyl group, a t-butyl group, a n-pentyl group and a n-hexyl group.

Examples of a $C_2$-$C_6$alkenyl group in the $C_2$-$C_6$alkenyl group which may be substituted with $G^1$ include a vinyl group, a n-propenyl group, an isopropenyl group, a butenyl group, a pentenyl group and a hexenyl group.

Examples of a $C_2$-$C_6$alkynyl group in the $C_2$-$C_6$alkynyl group which may be substituted with $G^1$ include an ethynyl group, a n-propynyl group, an isopropynyl group, a butynyl group, a pentynyl group and a hexynyl group.

Examples of an aromatic hydrocarbon group in the aromatic hydrocarbon group which may be substituted with $G^1$ include a phenyl group, a 1-naphthyl group and a 2-naphthyl group.

Likewise, examples of a heterocyclic group in the heterocyclic group which may be substituted with $G^1$ include a 5- or 6-membered saturated or unsaturated heterocyclic group or a condensed heterocyclic group, each of which contains 1 to 4 heteroatoms selected from an oxygen atom, a nitrogen atom and a sulfur atom as ring member(s).

Specific examples include (i) 5-membered saturated heterocyclic groups, (ii) 5-membered unsaturated heterocyclic groups, (iii) 6-membered saturated heterocyclic groups, (iv) 6-membered unsaturated heterocyclic groups and (v) condensed heterocyclic groups, as shown below.

(i) 5-Membered Saturated Heterocyclic Groups

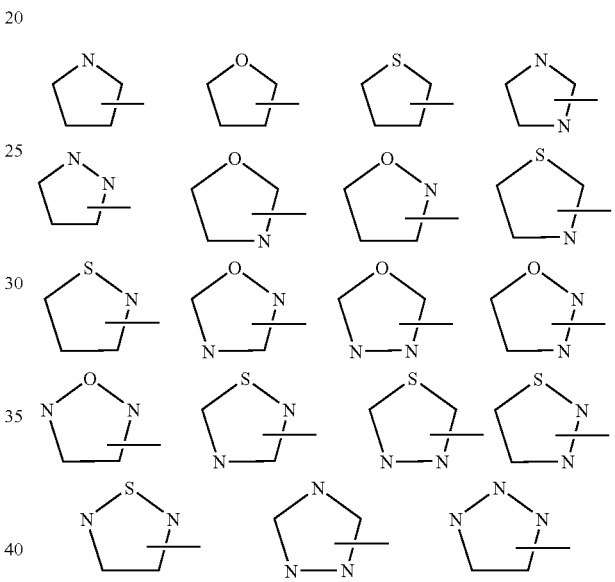

(ii) 5-Membered Unsaturated Heterocyclic Groups

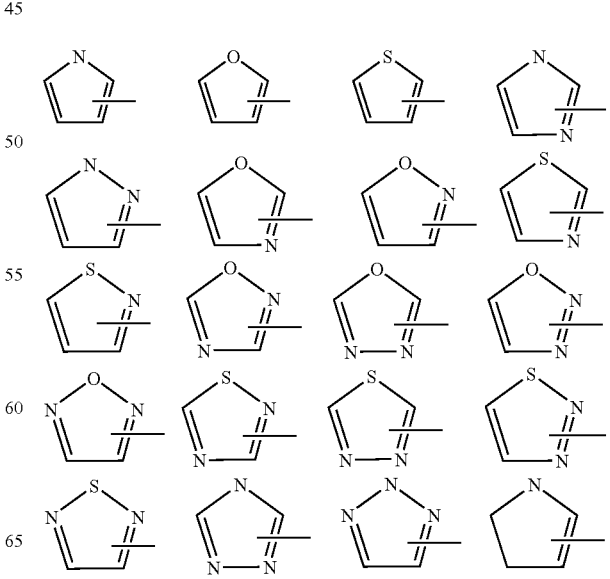

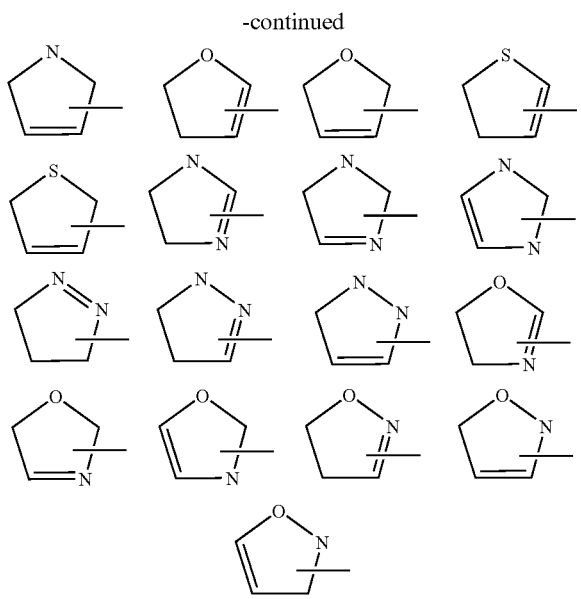

(iii) 6-Membered Saturated Heterocyclic Groups

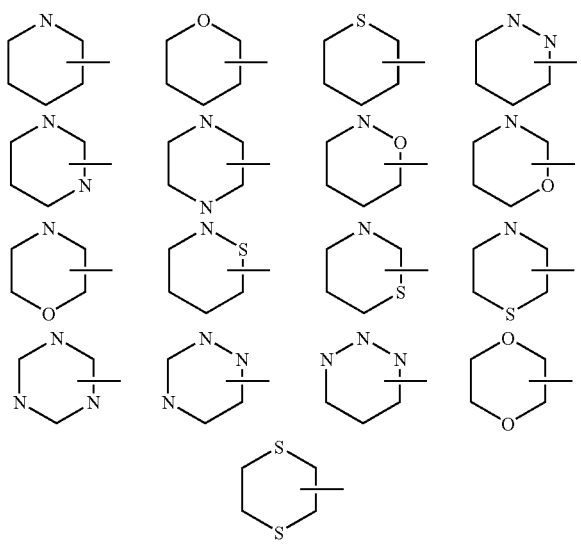

(iv) 6-Membered Unsaturated Heterocyclic Groups

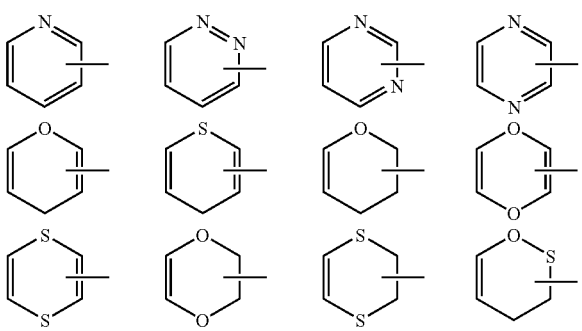

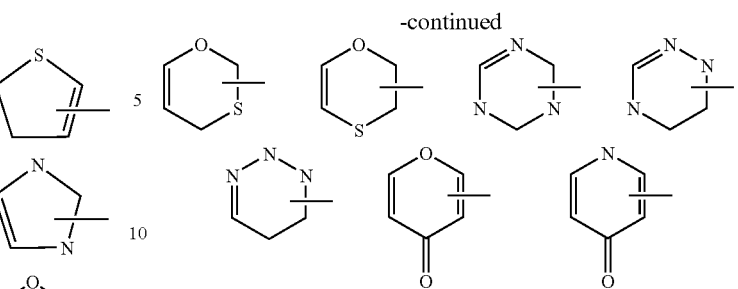

(v) Condensed Heterocyclic Groups

Quinolinyl groups such as quinolin-2-yl, quinolin-3-yl, quinolin-4-yl, quinolin-5-yl, quinolin-6-yl, quinolin-7-yl and quinolin-8-yl, as well as isoquinolinyl groups such as isoquinolin-1-yl, isoquinolin-3-yl, isoquinolin-4-yl, isoquinolin-5-yl, isoquinolin-6-yl, isoquinolin-7-yl and isoquinolin-8-yl.

Examples of $G^1$ include a hydroxy group; a nitro group; a cyano group; a halogen atom (e.g., a fluorine atom, a chlorine atom, a bromine atom); a $C_1$-$C_6$alkoxy group (e.g., a methoxy group, an ethoxy group, a n-propoxy group, an isopropoxy group, a n-butoxy group, a t-butoxy group); a trialkylsilyloxy group (e.g., a trimethylsilyloxy group, a triethylsilyloxy group, a t-butyldimethylsilyloxy group); a $C_1$-$C_6$alkylthio group (e.g., a methylthio group, an ethylthio group, a n-propylthio group, an isopropylthio group); a $C_1$-$C_6$alkylsulfinyl group (e.g., a methylsulfinyl group, an ethylsulfinyl group, a n-propylsulfinyl group); a $C_1$-$C_6$alkylsulfonyl group (e.g., a methylsulfonyl group, an ethylsulfonyl group, a n-propylsulfonyl group, an isopropylsulfonyl group, a n-butylsulfonyl group); an amino group substituted with a $C_1$-$C_6$alkyl group (e.g., a methylamino group, an ethylamino group, a n-propylamino group, an isopropylamino group); an amino group substituted with two $C_1$-$C_6$alkyl groups (e.g., a dimethylamino group, a diethylamino group, a methylethylamino group); a $C_1$-$C_6$alkylcarbonyl group (e.g., an acetyl group, a propionyl group, a propylcarbonyl group); and a $C_1$-$C_6$alkoxycarbonyl group (e.g., a methoxycarbonyl group, an ethoxycarbonyl group, a n-propylcarbonyl group, a t-butylcarbonyl group). The substituent $G^1$ may be attached at any position. Alternatively, the same or different substituents $G_1$ may be attached at several positions.

In the above Formula (1), B represents an optionally substituted $C_1$-$C_{20}$alkyl group, an optionally substituted $C_2$-$C_{20}$alkenyl group, an optionally substituted $C_2$-$C_{20}$alkynyl group, an optionally substituted aryl group or an optionally substituted heterocyclic group.

Specific examples of the above optionally substituted $C_1$-$C_{20}$alkyl group include:

$C_1$-$C_{20}$alkyl groups, such as a methyl group, an ethyl group, a n-propyl group, an isopropyl group, a n-butyl group, an isobutyl group, a sec-butyl group, a t-butyl group, a n-pentyl group, a neopentyl group, a n-hexyl group, an isohexyl group, a n-heptyl group, a n-octyl group, a n-nonyl group and a n-decyl group;

$C_1$-$C_{20}$alkyl groups substituted with oxygen-containing substituent(s), such as a methoxymethyl group, an ethoxymethyl group, a 2-methoxyethyl group, a 3-methoxypropyl group and a 4-methoxybutyl group;

$C_1$-$C_{20}$alkyl groups substituted with sulfur-containing substituent(s), such as a methylthiomethyl group, an ethylthiomethyl group, a 2-methylthioethyl group, a 3-methylthiopropyl group and a 4-methylthiobutyl group;

$C_1$-$C_{20}$alkyl groups substituted with nitrogen-containing substituent(s), such as a dimethylaminomethyl group, a diethylaminomethyl group and a 2-dimethylaminoethyl group; and $C_1$-$C_{20}$alkyl groups substituted with halogen atom(s), such as a fluoromethyl group, a chloromethyl group, a bromomethyl group, a difluoromethyl group, a dichloromethyl group, a difluoromethyl group, a trifluoromethyl group, a trichloromethyl group, a 2,2,2-trifluoroethyl group, a pentafluoroethyl group, a heptafluoropropyl group, a perfluorobutyl group and a perfluoropentyl group.

Examples of a substituent in the optionally substituted $C_2$-$C_{20}$alkenyl group or the optionally substituted $C_2$-$C_{20}$alkynyl group include an oxygen-containing substituent, a nitrogen-containing substituent, a sulfur-containing substituent, and a halogen atom. On the other hand, examples of a $C_2$-$C_{20}$alkenyl or alkynyl group include the same groups as listed above for $G^1$.

Examples of the above optionally substituted aryl group include a phenyl group, a 4-methylphenyl group, a 2-chlorophenyl group, a 4-chlorophenyl group, a 3-methoxyphenyl group, a 2,4-dimethylphenyl group, a 1-naphthyl group, a 2-naphthyl group, a 4-chloro-1-naphthyl group and a 6-methyl-2-naphthyl group.

The above optionally substituted heterocyclic group may be either a monocyclic heterocyclic group or a condensed heterocyclic group as long as it is a heterocyclic group containing 1 to 4 nitrogen atoms, oxygen atoms or sulfur atoms as ring member(s). Among them, preferred are a 5-membered heterocyclic ring, a 6-membered heterocyclic ring and a condensed heterocyclic group, each of which contains 1 to 4 nitrogen atoms, oxygen atoms or sulfur atoms. Specific examples include the same heterocyclic groups as listed above for $r^2$, $r^3$, $r^5$, $r^6$, $r^7$ and $r^8$.

Examples of a substituent on the heterocyclic group defined for B include a nitro group; a cyano group; a halogen atom (e.g., a fluorine atom, a chlorine atom, a bromine atom, an iodine atom); a $C_1$-$C_6$alkoxy group (e.g., a methoxy group, an ethoxy group, a n-propoxy group, an isopropoxy group, a n-butoxy group, a t-butoxy group); a $C_1$-$C_6$alkylthio group (e.g., a methylthio group, an ethylthio group, a n-propylthio group, an isopropylthio group, a n-butylthio group, a t-butylthio group); a $C_1$-$C_6$alkylsulfinyl group (e.g., a methylsulfinyl group, an ethylsulfinyl group, a n-propylsulfinyl group, an isopropylsulfinyl group, a n-butylsulfinyl group, a t-butylsulfinyl group); a $C_1$-$C_6$alkylsulfonyl group (e.g., a methylsulfonyl group, an ethylsulfonyl group, a n-propylsulfonyl group, an isopropylsulfonyl group, a n-butylsulfonyl group, a t-butylsulfonyl group); an amino group substituted with one $C_1$-$C_6$alkyl group (e.g., a methylamino group, an ethylamino group, a n-propylamino group); an amino group substituted with two $C_1$-$C_6$alkyl groups (e.g., a dimethylamino group, a diethylamino group, a dipropylamino group, an ethylmethylamino group, a methylpropylamino group); a $C_1$-$C_6$alkylcarbonyl group (e.g., an acetyl group, a propionyl group); a $C_1$-$C_6$alkoxycarbonyl group (e.g., a methoxycarbonyl group, an ethoxycarbonyl group, a n-propoxycarbonyl group, an isopropoxycarbonyl group, a n-butoxycarbonyl group, a t-butoxycarbonyl group); an optionally substituted phenylsulfinyl group; an optionally substituted phenylsulfonyl group; and an optionally substituted phenylthio group. Two or more of these substituents, which may be the same or different, may be substituted at any position on the heterocyclic ring.

Examples of a substituent on the above phenylsulfinyl group, phenylsulfonyl group or phenylthio group include a halogen atom (e.g., a fluorine atom, a chlorine atom, a bromine atom); a $C_1$-$C_6$alkyl group (e.g., a methyl group, an ethyl group); a $C_1$-$C_6$haloalkyl group (e.g., a trifluoromethyl group, a 2,2,2-trifluoroethyl group, a pentafluoroethyl group); and a $C_1$-$C_6$haloalkoxy group (e.g., a trifluoromethoxy group, a 2,2,2-trifluoroethoxy group, a pentafluoroethoxy group).

(b) Polar Organic Solvent

The polar organic solvent used in the present invention is not limited in any way as long as it is an organic solvent composed of molecules having a dipole moment. Examples include an ether solvent, a ketone solvent, a halogenated hydrocarbon solvent, a nitrile solvent, an amide solvent, a urea solvent, an ester solvent, a sulfur-containing solvent, and a halogenated aromatic hydrocarbon solvent.

Specific examples include ether solvents such as diethylether, tetrahydrofuran, 1,2-dimethoxyethane and 1,4-dioxane; ketone solvents such as acetone, methylethylketone, methylisobutylketone and cyclohexanone; halogenated hydrocarbon solvents such as dichloromethane, chloroform, carbon tetrachloride and 1,2-dichloroethane; nitrile solvents such as acetonitrile and benzonitrile; amide solvents such as N,N-dimethylformamide, N,N-dimethylacetamide, N-methylpyrrolidone and hexamethylphosphoramide; urea solvents such as 1,3-dimethyl-2-imidazolidinone; ester solvents such as methyl acetate, ethyl acetate and n-propyl acetate; sulfur-containing solvents such as dimethyl sulfoxide and sulfolane; as well as halogenated aromatic hydrocarbon solvents such as chlorobenzene, chlorotoluene, dichlorotoluene and chloroxylene. The polar organic solvent solution of the present invention may also comprise two or more of these polar organic solvents.

Among them, preferred is a polar organic solvent that is available for dissolving both the organic compound and water and that can be readily distilled off together with water. Examples of such a polar organic solvent include an ether solvent and a ketone solvent. When using these solvents, it is preferable to apply the method of the present invention. Among them, an ether solvent is more preferred for use and tetrahydrofuran is particularly preferred for use.

(c) Water

Since there is no particular limitation on the amount (concentration) of water contained in the polar organic solvent solution used in the present invention, the method of the present invention can be applied even when using a polar organic solvent solution rich in water (e.g., containing 50% by weight or more of water). Preferably, such a water-rich polar organic solvent solution may be treated using other operations (e.g., partition) to reduce its water content before being provided for the method of the present invention.

(d) Halogen Compound

The method of the present invention can preferably be used in a case where the above polar organic solvent solution contains an organic compound, water and a compound which produces, upon coming into contact with water or an alcohol solvent, a substance accelerating the decomposition of the organic compound. A typical example of a substance accelerating the decomposition of the organic compound is a halogen compound.

Examples of such a halogen compound include a halogen (a simple substance; e.g., chlorine, bromine, iodine); a metal halogen compound (e.g., a metal chloride, a metal bromide, a metal iodide); and an organic halogen compound (e.g., an organic chloride, an organic bromide, an organic iodide). Among these halogen compounds, the method of the present invention is particularly effective when the reaction system contains iodine or an alkali metal iodine compound. Examples of an alkali metal iodine compound include lithium iodide, sodium iodide, potassium iodide, magnesium iodide, calcium iodide, ferric iodide, zinc iodide, and cupric iodide.

Although the above polar organic solvent solution is not limited in any way as long as it contains an organic compound and water, it is preferably a reaction solution obtained by reacting a compound of the above Formula (2) with a 4-halogenomethyldioxolenone compound of the above Formula (3) in a polar organic solvent, or a solution obtained by working up the reaction solution (e.g., by washing the reaction solution with water or the like and then collecting the organic layer). In the present invention, the latter solution is preferred because the present invention is preferably intended to ensure a higher yield in isolating a target organic compound.

In the above Formula (2), A is as defined above.

M represents a hydrogen atom; an alkali metal such as lithium, sodium or potassium; an alkaline earth metal such as magnesium or calcium; or a transition metal such as copper(I), copper(II), cobalt(II), cobalt(III), iron (II), iron (III), zinc(II) or manganese(II). In a case where M represents an atom other than hydrogen, a compound of Formula (2) may be in either anhydride or hydrate form.

In the above Formula (3), $R_1$ and $R_2$ each independently represent a hydrogen atom, an optionally substituted $C_1$-$C_6$alkyl group or an optionally substituted phenyl group.

Examples of a $C_1$-$C_6$alkyl group include a methyl group, an ethyl group, a n-propyl group, an isopropyl group, a n-butyl group, a sec-butyl group, a t-butyl group, a n-pentyl group and a n-hexyl group.

Examples of a substituent on the above $C_1$-$C_6$alkyl group or phenyl group include a nitro group; a cyano group; a halogen atom (e.g., a fluorine atom, a chlorine atom, a bromine atom, an iodine atom); a $C_1$-$C_6$alkoxy group (e.g., a methoxy group, an ethoxy group, a n-propoxy group, an isopropoxy group, a n-butoxy group, a t-butoxy group); a $C_1$-$C_6$alkylthio group (e.g., a methylthio group, an ethylthio group, a n-propylthio group, an isopropylthio group, a n-butylthio group, a t-butylthio group); a $C_1$-$C_6$alkylsulfinyl group (e.g., a methylsulfinyl group, an ethylsulfinyl group); a $C_1$-$C_6$alkylsulfonyl group (e.g., a methylsulfonyl group, an ethylsulfonyl group, a n-propylsulfonyl group, an isopropylsulfonyl group, a n-butylsulfonyl group, a t-butylsulfonyl group); an amino group substituted with one $C_1$-$C_6$alkyl group (e.g., a methylamino group, an ethylamino group, a n-propylamino group); an amino group substituted with two $C_1$-$C_6$alkyl groups (e.g., a dimethylamino group, a diethylamino group); a $C_1$-$C_6$alkylcarbonyl group (e.g., an acetyl group, a propionyl group); a $C_1$-$C_6$alkoxycarbonyl group (e.g., a methoxycarbonyl group, an ethoxycarbonyl group); as well as a phenylsulfinyl group which may be substituted with $G^2$, a phenylsulfonyl group which may be substituted with $G^2$, and a phenylthio group which may be substituted with $G^2$.

Examples of $G^2$ include a halogen atom (e.g., a fluorine atom, a chlorine atom, a bromine atom); a $C_1$-$C_6$alkyl group (e.g., a methyl group, an ethyl group); a $C_1$-$C_6$haloalkyl group (e.g., a trifluoromethyl group); and a $C_1$-$C_6$haloalkoxy group (e.g., a trifluoromethoxy group).

Alternatively, $R_1$ and $R_2$ may together form an optionally substituted $C_3$-$C_8$ring. Examples of a $C_3$-$C_8$ring include a cyclopentene ring, a cyclohexene ring, a cycloheptene ring and a cyclooctene ring. Examples of a substituent on the above ring include a $C_1$-$C_6$alkyl group (e.g., a methyl group, an ethyl group); a $C_1$-$C_6$alkoxy group (e.g., a methoxy group, an ethoxy group, a n-propoxy group, an isopropoxy group, a n-butoxy group, a t-butoxy group); a halogen atom (e.g., a fluorine atom, a chlorine atom); a $C_1$-$C_6$alkylthio group (e.g., a methylthio group, an ethylthio group); a substituted amino group (e.g., a dimethylamino group, an acetylamino group); a nitro group; and a cyano group. One or more of these substituents, which may be the same or different, may be substituted at any position.

Among them, preferred as $R_1$ and $R_2$ is a hydrogen atom or a $C_1$-$C_6$alkyl group, and particularly preferred is a hydrogen atom or a methyl group.

The following may be mentioned as specific examples of a preferred 4-halogenomethyldioxolenone compound of the above Formula (3):

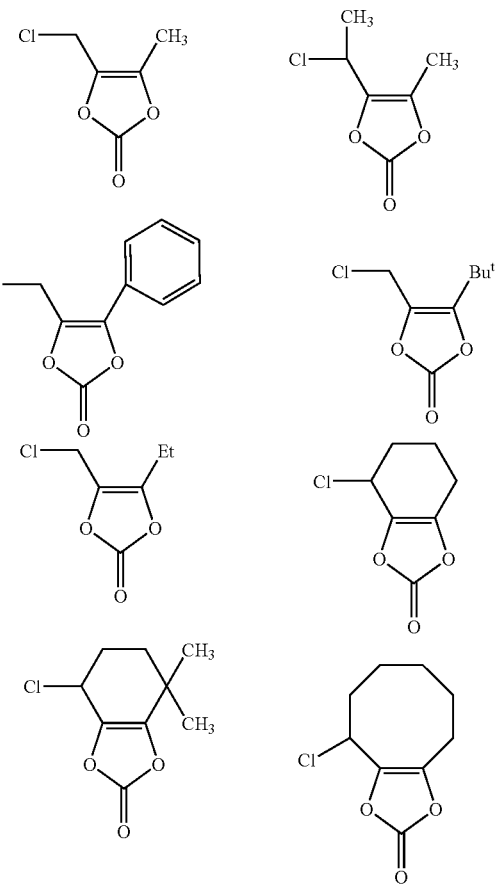

A 4-halogenomethyldioxolenone compound of the above Formula (3) may be prepared and obtained, for example, by the method described in U.S. Pat. No. 4,448,732.

In the reaction between a compound of the above Formula (2) and a 4-halogenomethyldioxolenone compound of the above Formula (3), a phase-transfer catalyst may be added for smooth progress of the reaction. Examples of such a phase-transfer catalyst include quarternary ammonium salts, such as tetraalkylammonium chlorides (e.g., tetramethylammonium chloride, tetraethylammonium chloride, tetrapropylammonium chloride, tetrabutylammonium chloride (TBAC)); tetraalkylammonium bromides (e.g., tetramethylammonium bromide, tetraethylammonium bromide, tetrapropylammonium bromide, tetrabutylammonium bromide); and benzyltrialkylammonium halides (e.g., benzyltrimethylammonium chloride, benzyltrimethylammonium bromide, benzyl-tri-n-butylammonium chloride (BTBAC), benzyl-tri-n-butylammonium bromide).

In the above reaction, when M in the above Formula (2) represents a hydrogen atom (i.e., the compound of Formula (2) is a carboxylic acid), it is preferable to add a base to the reaction system. Examples of a base available for use include an alkali metal hydroxide (e.g., sodium hydroxide, potassium hydroxide); an alkaline earth metal hydroxide (e.g., magnesium hydroxide, calcium hydroxide); an alkali metal carbonate salt (e.g., sodium carbonate, potassium carbonate); an alkali metal bicarbonate salt (e.g., sodium bicarbonate, potassium bicarbonate); an alkaline earth metal carbonate salt (e.g., magnesium carbonate, calcium carbonate); a metal hydride (e.g., sodium hydride, calcium hydride); a metal alkoxide (e.g., sodium methoxide, sodium ethoxide, potassium t-butoxide, magnesium methoxide, magnesium ethoxide); and an organic base (e.g., triethylamine, pyridine).

2) Dehydration Step

When the above polar organic solvent solution is distilled to remove water together with the polar organic solvent to obtain an organic compound solution whose concentration of water is below a given level, the present invention is characterized by (a) distilling off water together with the polar organic solvent while continuously adding a polar organic solvent to the above solution, or by (b) repeating several cycles of adding a given amount of a polar organic solvent to the above solution and then distilling off water together with the polar organic solvent from the above solution. It has been found that by using the above procedure (a) or (b), changes in the liquid level in a vessel can be avoided and hence the adhesion of a highly concentrated solution onto the vessel wall surface can be prevented. Consequently, the highly concentrated solution can be prevented from being heated and becoming decomposed on the vessel wall surface.

The polar solvent to be added during the dehydration step may be the same as or different from the polar solvent contained in the above solution. Specific examples include the same polar solvents as listed above for those contained in the above solution.

In the present invention, it is possible to use either of the above procedure (a) or (b). If the position of the liquid interface (horizontal surface) of the solution changes during the dehydration step, the residue of the solution will be heated more than necessary in a local area with a lowered interface position to increase the risk of producing a compound accelerating the decomposition of the organic compound, thus facilitating the decomposition of the organic compound. For this reason, a heating area of the vessel is preferably kept at substantially the same position as that of the current liquid interface or at a lower position. In order to minimize changes in the liquid interface caused by distillation of the solution, the amount of a polar organic solvent to be added is preferably set to substantially the same amount (volume) as that of the distilled-off polar organic solvent and water.

The dehydration step may be accomplished in a vessel containing the above solution. In a case where the above solution is a reaction solution, the dehydration step may be performed continuously after completion of the reaction in the reaction vessel used for the reaction. Alternatively, a reaction solution may also be transferred to another vessel before being subjected to the dehydration step.

To distill off water together with the polar organic solvent from the above solution, a vessel may be heated to a given temperature. The heating temperature in a vessel will vary also depending on the type of polar organic solvent. A higher heating temperature in a vessel will improve the work efficiency of the dehydration step, but too high a heating temperature can facilitate the decomposition of the organic compound. Thus, the polar organic solvent and water are preferably distilled off at as low temperature as possible by heating in a vacuum in order to ensure a higher efficiency in distilling off the polar organic solvent and water while preventing the decomposition of the organic compound.

Although the heating temperature for the solution and the degree of vacuum in a vessel during the dehydration step can be determined according to, e.g., the boiling point of the polar organic solvent to be used and the heat stability of the organic compound, it usually ranges from 0° C. to 80° C., preferably 10° C. to 70° C., and more preferably 20° C. to 50° C. The internal pressure of the vessel during heating ranges from 1 to 100 kPa, and preferably 10 to 50 kPa.

Also, the dehydration step is preferably accomplished in a vessel equipped with known distillation equipment. The distillation equipment is not limited in any way as long as it allows collection of the distilled-off polar organic solvent and water. For example, distillation equipment having a piping system, a condenser tube and a collector may be used for this purpose.

In the solution after the dehydration step, water should be removed to the extent that the target organic compound can be obtained in high isolated yield. The water content in the solution after the dehydration step is usually 4% by weight or less, preferably 3.5% by weight or less, based on the total weight of the solution after the dehydration step. The water content in the solution after the dehydration step can be measured using a known water content meter (e.g., a Karl-Fisher titrator).

3) Crystallization Step

The organic compound is then isolated from the solution whose water content reaches below a given level.

Techniques used for isolation of the organic compound include, for example, those involving: (i) distilling off the polar organic solvent from the solution obtained in the dehydration step, and then adding a crystallization solvent to the residue to effect crystallization; (ii) distilling off the polar organic solvent from the solution obtained in the dehydration step while supplementing the solution with a crystallization solvent to crystallize the organic compound; (iii) adding a recrystallization solvent to the residue to effect recrystallization; or (iv) purifying the residue by the technique of column chromatography. As used herein, the term "crystallization solvent" is intended to mean an organic solvent having a low solubility to the organic compound and preferably having a high solubility to impurities, as specifically exemplified by solvents used for recrystallization (recrystallization solvents) and solvents having a considerably low solubility to the organic compound to be crystallized (generally referred to as "poor solvents"). The distinction between poor solvents and recrystallization solvents is not precise; which of them is used depends on the circumstances.

Among these techniques, (i) or (ii) is preferred for use and (ii) is particularly preferred. Moreover, techniques (i) and (ii) allow greater reduction in the amount of a crystallization solvent to be used when compared to other techniques.

15

In the above technique (ii), to supplement the solution with a crystallization solvent, a given amount of the crystallization solvent may be added in divided portions or continuously at a constant rate, either of which may be used in the present invention. However, when the volume of the solution is reduced during the crystallization step, the solution is more likely to be concentrated locally at the liquid interface. For this reason, in order to maintain the liquid interface of the solution at a constant position, the amount of a crystallization solvent to be added is preferably set to substantially the same amount (volume) as that of the distilled-off polar organic solvent.

Although the crystallization solvent to be used is not limited in any way as long as it is a solvent having a low solubility to the organic compound and allowing stable existence of the organic compound without causing its decomposition, an alcohol solvent is preferred for use.

Examples of an alcohol solvent include $C_1$-$C_6$-alcohols such as methanol, ethanol, n-propyl alcohol, isopropyl alcohol, n-butyl alcohol, sec-butyl alcohol, and t-butyl alcohol. Among them, $C_1$-$C_3$-alcohols are preferred for use and ethanol is particularly preferred for use.

The crystallization step may be effected continuously in the same vessel where the above dehydration step has been performed. Alternatively, the solution obtained in the dehydration step may also be transferred to another vessel where the crystallization step will be performed.

The crystallization step may be accomplished by heating a vessel to distill off the polar organic solvent. The heating temperature in a vessel will vary also depending on the type of polar organic solvent. A higher heating temperature will improve the work efficiency of the solvent replacement step, but too high a heating temperature can facilitate the decomposition of the organic compound. Thus, a vessel is preferably heated in a vacuum in order to ensure a higher efficiency in distilling off the polar organic solvent at as low temperature as possible.

The solution temperature in the crystallization step usually ranges from 0° C. to 80° C., preferably 10° C. to 70° C., and more preferably 20° C. to 50° C. The internal pressure of the vessel during heating ranges from 1 to 100 kPa, and preferably 5 to 50 kPa.

The concentration of the polar organic solvent in the solution after the crystallization step is usually 5% by weight or less, preferably 3% by weight or less, and more preferably 1% by weight or less.

Once removal of the polar organic solvent has been completed, the resulting solution may be cooled to 10° C. or below, preferably 0° C. to 10° C., to crystallize the target organic compound. The cooling time required for crystallization usually ranges from several tens of minutes to several hours.

The precipitated organic compound may be isolated, e.g., by filtration or using a centrifugal separator to remove the crystallization solvent. The resulting organic compound may be subject to recrystallization or washed with the same solvent as used for recrystallization or crystallization, if desired.

According to the procedures described above, the target organic compound can be efficiently isolated. The structure of the resulting organic compound may be confirmed by measuring its IR spectrum, mass spectrum and $^1$H-NMR spectrum or by gas chromatography, high performance liquid chromatography, etc.

EXAMPLES

The present invention will now be further described in more detail in the following examples, which are not intended to limit the scope of the invention.

In the examples and comparative examples shown below, the starting material (5R,6S)-6-(1-(R)-hydroxyethyl)-7-oxo-3-(2-(R)-tetrahydrofuryl)-4-thia-1-azabicyclo[3.2.0]hept-2-ene-2-carboxylic acid sodium salt 2.5-hydrate was prepared according to the method described in JP 63-162694 A.

Example 1

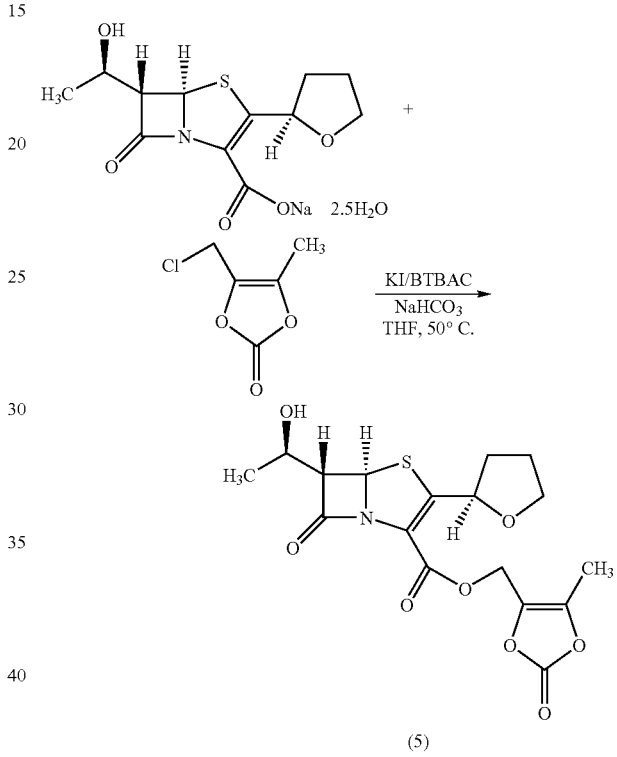

(5)

(5R,6S)-6-(1-(R)-Hydroxyethyl)-7-oxo-3-(2-(R)-tetrahydrofuryl)-4-thia-1-azabicyclo[3.2.0]hept-2-ene-2-carboxylic acid sodium salt 2.5-hydrate (111.0 g, purity: 98.4%), potassium iodide (5.15 g), sodium bicarbonate (2.60 g) and BTBAC (3.87 g) were mixed in THF (465 ml). To this mixture, 4-chloromethyl-5-methyl-2-oxo-1,3-dioxolene (50.48 g, purity: 97.2%) was added and stirred at 30° C. for 2 hours and then at 55° C. for 4 hours. After completion of the reaction, the reaction solution was washed once with water (155 ml) and twice with 20% aqueous sodium chloride (155 ml) which had been adjusted to pH 8 with potassium bicarbonate, followed by isolating the organic layer. In this way, a β-lactam compound solution (534.7 g, hereinafter referred to as "Solution A") was obtained, which contained a β-lactam compound of Formula (5) (hereinafter referred to as "Compound (5)"), iodine compounds, water and THF. By quantitative analysis using high performance liquid column chromatography, Solution A was found to contain the target Compound (5) in an amount of 22.44% by weight (yield: 97.4%). The water content in Solution A was about 4% by weight.

Solution A thus obtained was placed in a vacuum of 17.3 to 19.3 kPa and at a temperature of 20° C. to 32° C. (bath temperature: 40° C.) to distill off THF. Whenever about 90 ml of THF was distilled off, Solution A was supplemented with 90 ml fresh THF. This procedure was repeated three times. In this way, a THF solution of Compound (5) was obtained. The resulting solution was a 0.9 L/mol solution of Compound (5). When the water content in Solution A was measured, it was 0.47% by weight.

Solution A was then warmed to 75° C. and THF was distilled off to give a concentrated THF solution of Compound (5) (about 0.25 L/mol in THF), followed by addition of ethanol (95 ml). The resulting solution was stirred to give a homogenous solution and placed in a vacuum of 16 to 20 kPa at 23° C. to 40° C. (bath temperature: 23° C. to 40° C.) to distill off THF and ethanol. At this time, ethanol was added dropwise at a constant speed to keep the solution volume unchanged, thus obtaining Solution B. The total amount of ethanol added dropwise was 105 ml. Solution B was a 1.2 L/mol solution of Compound (5).

Solution B was then cooled to 15° C. for 30 minutes to crystallize Compound (5). The precipitated crystals were collected by filtration and washed twice with cold ethanol (12 ml). The resulting crystals were dried to give crude crystals of Compound (5) (35.65 g) in 98.9% purity and 88.7% yield.

The crude crystals of Compound (5) were suspended in ethanol (180 ml) and heated at 60° C. for 10 minutes to completely dissolve the crystals. After this solution was filtered under pressure, the resulting filtrate was held at around 30° C. for 30 minutes and then placed in a vacuum of 10.6 to 13.3 kPa at 30° C. to 35° C. to distill off 80 ml ethanol. The resulting solution was then cooled at 15° C. for 30 minutes to crystallize Compound (5). The crystallized crystals were collected by filtration and washed twice with cold ethanol (13 ml) to give crystals of Compound (5) in 99.5% purity and 85.1% yield.

Example 2

The same procedure as shown in Example 1 was repeated, except that the step of distilling off THF from Solution A in a vacuum in Example 1 was replaced by the step of distilling off THF while adding dropwise THF through a nozzle reaching near the surface of Solution A. This example produced substantially the same results as Example 1.

Comparative Example 1

In the step of distilling off THF from Solution A in Example 2, THF was added in one portion (not continuously) prior to distillation. The water content in the solution after distilling off THF was 2% by weight. Subsequently, the same procedure as shown in Example 1 was repeated to isolate Compound (5). Compound (5) was obtained in the same purity as Example 1, but its yield was reduced to as low as 80%.

Comparative Example 2

The same procedure as shown in Comparative Example 1 was repeated to isolate Compound (5), except that the step of distilling off THF in Comparative Example 1 was followed by addition of ethanol in one portion (not continuously) to distill off ethanol and THF. Compound (5) was obtained in the same purity as Example 1, but its yield was reduced to as low as 70%. In this case, the mother liquor was found to contain Compound (5) in an amount corresponding to the reduction in yield. When the mother liquor was analyzed for its solvent composition, THF was found to remain in a large amount, which would lead to the reduction in yield because Compound (5) could dissolve in THF. When the amount of ethanol added in one portion was increased 3-fold and the same procedure was repeated, the same results as observed in Comparative Example 1 were obtained for both purity and yield, but the amount of the solvent used was increased.

INDUSTRIAL APPLICABILITY

The present invention requires a shorter time for removal of water from a polar organic solvent solution, thus enabling prevention of prolonged heating and hence decomposition of an organic compound in a water-rich polar organic solvent, and also enabling efficient isolation of the organic compound in high isolated yield. Moreover, when the polar organic solvent is distilled off while adding a crystallization solvent, it is possible to reduce the total amount of the crystallization solvent to be used. This is advantageous in terms of production costs.

The invention claimed is:

1. A method for preparing a β-lactam compound, which comprises the following steps:

reacting a compound of Formula (2),

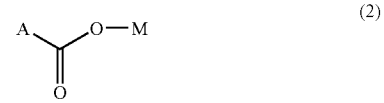

wherein A represents a condensed heterocyclic group having a β-lactam ring structure, and M represents a hydrogen atom or a metal atom, in a polar organic solvent, with a 4-halogenomethyldioxolenone compound of Formula (3),

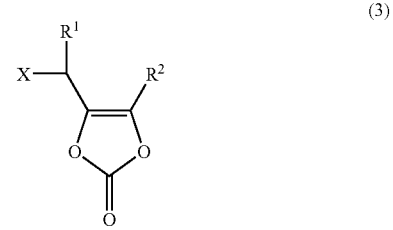

wherein $R^1$ and $R^2$ each independently represent a hydrogen atom, an optionally substituted $C_1$-$C_6$ alkyl group or an optionally substituted phenyl group, or $R^1$ and $R^2$ together form an optionally substituted $C_3$-$C_8$ ring, and X represents a halogen atom, to result in a reaction solution containing a β-lactam compound in the polar organic solvent;

dehydrating a polar organic solvent solution obtained as the reaction solution or obtained by working up the reaction solution, to bring the concentration of water below a given level, wherein the dehydration step comprises distilling off water together with the polar organic solvent while adding a polar organic solvent to the solution, or comprises repeating two or more cycles of adding a polar organic solvent to the polar organic solvent solution and then distilling off water together with the polar organic solvent wherein the polar organic solvent further contains an iodine compound.

2. The method for preparing a β-lactam compound according to claim 1, wherein the iodine compound is iodine or a metal iodide.

3. The method for preparing a β-lactam compound according to claim 1, wherein the polar organic solvent solution is a solution in an ether solvent or a ketone solvent.

4. The method for preparing a β-lactam compound, which comprises the dehydration step according to claim 1, wherein the dehydration step is followed by a crystallization step of distilling off the polar organic solvent from the resulting solution while supplementing the solution with a poor solvent for the organic compound so as to crystallize the organic compound.

5. The method for preparing a β-lactam compound according to claim 4, wherein an alcohol solvent is used as the poor solvent.

* * * * *